United States Patent [19]

Wilkes et al.

[11] 4,022,823
[45] May 10, 1977

[54] CITRIC ACID AND CITRAMALIC ACID PREPARATION

[75] Inventors: John B. Wilkes, Richmond; Robert G. Wall, Pinole, both of Calif.

[73] Assignee: Chevron Research Company, San Francisco, Calif.

[22] Filed: Apr. 26, 1976

[21] Appl. No.: 680,396

Related U.S. Application Data

[63] Continuation-in-part of Ser. No. 491,987, July 29, 1974, abandoned, which is a continuation-in-part of Ser. No. 303,730, Nov. 6, 1972, abandoned, which is a continuation-in-part of Ser. No. 150,859, June 1, 1971, abandoned.

[52] U.S. Cl. .................... 260/531 R; 260/535 P
[51] Int. Cl.$^2$ ................................. C07B 3/00
[58] Field of Search ............ 260/531 R, 533, 535 P

[56] References Cited

UNITED STATES PATENTS

| | | | |
|---|---|---|---|
| 2,847,464 | 8/1958 | Robertson et al. | 260/533 R |
| 2,867,657 | 1/1959 | Selwitz | 260/531 R |
| 3,5171059 | 6/1970 | Volker et al. | 260/533 R |

OTHER PUBLICATIONS

"Nitrogen Teroxide", Hercules bulletin (1968) pp. 34-61.

Primary Examiner—Richard L. Raymond
Attorney, Agent, or Firm—Dix A. Newell; John Stoner, Jr.; W. Keith Turner

[57] ABSTRACT

A process for the preparation of citric acid which comprises contacting an unsaturated compound selected from 3-methylene-1,5-pentanediol and its esters with a nitric acid solution in an amount of 2 to 50 mols of nitric acid feed per mol of unsaturated compound feed, and at least 0.005 mol percent nitrogen dioxide based on nitric acid, at a temperature between −10° and 120° C., to thereby oxidize said unsaturated compound to citric acid. Preferably the contacting of the unsaturated compound so as to synthesize citric acid is carried out in the absence of any substantial amount of vanadium as the presence of vanadium catalysts has been found to effectively prevent the recovery of good yields of citric acid from the process.

The citric acid synthesis preferably is carried out by an overall process wherein isobutene is reacted with two mols of formaldehyde to produce 3-methylene-1,5-pentanediol, which is then converted to citric acid by reaction with nitrogen dioxide/nitric acid.

Citramalic production from 3-methyl-3-buten-1-ol is also disclosed.

48 Claims, No Drawings a number 4,022,823

CITRIC ACID AND CITRAMALIC ACID PREPARATION

CROSS-REFERENCE TO RELATED APPLICATIONS

This application is a continuation-in-part of copending application Ser. No. 491,987, filed July 29, 1974, now abandoned, which in turn is a continuation-in-part of application Ser. No. 303,730, filed Nov. 6, 1972, now abandoned, which in turn is a continuation-in-part of application Ser. No. 150,859, filed June 1, 1971, now abandoned. The disclosures of the earlier applications are incorporated herein by reference.

BACKGROUND OF THE INVENTION

The invention relates to a novel process for the production of citric acid from 3-methylene-1,5-pentanediol, and also to a novel process for production of citramalic acid from 3-methyl-3-buten-1-ol.

In addition to the substantial use of citric acid in soft drinks and other foods, sodium citrate appears to be an excellent replacement for the phosphate builders of the detergent art and various other uses for citric acid have been developing. However, the principal source for citric acid is from the fermentation of organic material such as molasses. Such a process is not completely satisfactory, especially where increasingly large amounts of citric acids are required.

Citric acid is a complex molecule having the following structure:

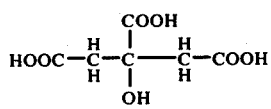

No commercial routes have been developed to date for the synthesis of the complex citric acid molecule. As pointed out in Chemical Week, April 10, 1974, at page 29, entitled "New Uses May Make Citric's Cup Run Over":

"Synthetic routes to citric also have been explored, but no commercially usable process have been devised. The citric molecule is extremely complex, requires too many steps for economic synthesis."

However, the present invention disclosed herein provides a process for making citric acid relatively inexpensively, and with few steps and commercially available feed.

The present invention concerns synthesis of citric acid from a feed material containing both olefin unsaturation and hydroxyl groups and using nitrogen dioxide and nitric acid. As used herein the term nitrogen dioxide includes its equivalent equilibrium form dinitrogen tetroxide. Art concerning olefin reactions with nitrogen dioxide and nitric acid teaches that the typical products of the reaction are nitro paraffins and nitro alcohols. Propylene and isobutene have been indicated to be exceptions to this general rule in that propylene can be oxidized with nitrogen dioxide and nitric acid to hydroxy acid, namely hydroxy propionic acid (lactic acid); and isobutene can be oxidized to alpha-hydroxy isobutyric acid. Thus, the work as reported by Levy and Scaife, J. Chem. Soc., London (1946), 1093, indicated that typically with higher olefins, that is olefins above isobutene, the normal reaction product with nitrogen dioxide and nitric acid is a dinitro paraffin. Levy and Scaife pointed out at page 1094:

"It has been found that, although ethylene and olefins [other than $C_3$ or $C_4$ olefins] such as octylenes and cyclohexene may be suitably nitrated in the absence of solvent, i.e., by addition to liquid tetroxide, yet propylene and the butylenes give rise to partly oxidized substances containing little or no dinitroparaffin unless an ether- or ester-type solvent is used."

Other pertinent art concerning reaction of olefins with nitrogen dioxide and/or nitric acid include: Muller et al. U.S. Pat. No. 3,324,168; a Russian article by B. F. Ustavshchikov et al., Doklady Akademii Nauk, S.S.S.R., Vol. 157, pp. 143–146, July 1964, entitled "On the Course of the Reaction of the Simplest Olefins with Liquid Nitrogen Tetroxide"; Gardner et al U.S. Pat. No. 2,847,453; Robertson et al. U.S. Pat. No. 2,847,465; and the brochure "Nitrogen Tetroxide" by Hercules, Incorporated, 1968.

Belgian Patent 775,729 to Washecheck discloses the oxidation of n-alkanol to a carboxylic acid using nitric acid. According to the Washecheck reference the saturated alcohols are advantageously oxidized with nitric acid using a vanadium catalyst.

The prior art does not appear to disclose treatment of any $C_6$ or similar unsaturated alcohol with nitrogen dioxide and nitric acid to obtain a polybasic hydroxy acid. Also the prior art discloses only complex routes for the synthesis of citric acid, see, for example, U.S. Pat. Nos. 3,356,721; U.S. 3,852,322; and U.S. 3,843,692.

According to another embodiment of the present invention citramalic acid is produced. Citramalic acid occurs naturally in many foods, e.g., apples, pears, bananas, etc. Synthetic citramalic acid has been made by condensation of hydrogen cyanide with ethyl acetoacetate, but this process is too expensive for commercial use. Citramalic acid is useful as an acidulant for soft drinks and the like. It is also useful in the production of citraconic acid and itaconic acid.

SUMMARY OF THE INVENTION

According to the present invention a process is provided for the preparation of citric acid which comprises contacting an unsaturated compound selected from 3-methylene-1,5-pentanediol and its esters with a nitric acid solution in an amount of 2 to 50 mols of nitric acid feed per mol of unsaturated compound feed, and at least 0.005 mol percent nitrogen dioxide based on nitric acid, at a temperature between −10° and 120° C., to thereby oxidize said unsaturated compound to citric acid.

According to a preferred embodiment of the present invention a simple overall synthesis is provided for producing citric acid which process comprises: (a) reacting isobutene with two mols of formaldehyde to obtain 3-methylene-1,5-pentanediol and (b) contacting the 3-methylene-1,5-pentanediol with a nitric acid solution in an amount of 2 to 50 mols of nitric acid feed per mol of 3-methylene-1,5-pentanediol, and at least 0.005 mol percent nitrogen dioxide based on nitric acid, at a temperature between −10° and 120° C, to thereby oxidize said 3-methylene-1,5-pentanediol to citric acid.

According to another embodiment of the present invention citramalic acid is produced by contacting an unsaturated compound selected from 3-methyl-3-buten-1-ol and its esters and formals with a nitric acid solution in an amount of 2 to 50 mols of nitric acid feed per mol of unsaturated compound feed, and at least 0.05 mol percent nitrogen dioxide based on nitric acid, at a temperature between −10° and 120° C, to thereby oxidize said unsaturated compound to citramalic acid.

We have found that citramalic acid is advantageously produced from 3-methyl-3-buten-1-ol in one or two stages using reaction conditions as described herein for citric acid production from the unsaturated diol. Citramalic salt or acid can be separated from the one or two stage crude product mixture by conventional methods.

Although the oxidation process of the present invention can be carried out in two stages, preferably one stage is used for the present process wherein both reaction of the diol with nitrogen dioxide and oxidation with nitric acid take place to a substantial extent or to completion in one reaction zone. In the two-stage oxidation of the present invention the main reaction in the first stage is that of the reaction of the feed with nitrogen dioxide and the reaction with nitric acid is subsequently carried out in a second stage.

One of the surprising features of the present invention is that we have found that the oxidation process of the present invention is advantageously carried out in a one-stage operation at a temperature of about 45° to 85° C.

Although the feed to the oxidation step of our process is not simply an olefin, our feed does contain an olefinic type unsaturation bond. Prior art suggests oxidation reactions of alpha olefins with nitrogen dixoide and nitric acid to give alpha-hydroxy carboxylic acids should be carried out using temperatures below 40° C., preferably below 20° C. The previously cited Russian reference suggests the use of temperatures between 0° and 10° C. Gardner et al. U.S. Pat. No. 2,847,453 suggests the use of temperatures below about 40° C., for example, 0° C. as in Examples 1, 2 and 3 of the Gardner et al. reference for the reaction of nitrogen dioxide in a 70 percent nitric acid solution with isobutene to obtain alpha-hydroxy isobutyric acid.

Also, the previously cited Washecheck reference concerning the oxidation of hydroxyl groups of alkanol feeds to carboxyl groups suggests the use of temperatures below about 40° C. in his nitric acid oxidation when he desires obtaining carboxylic acids of the same number of carbon atoms as the feed alkanol. At higher temperatures, particularly temperatures of 60° C. and higher, Washecheck obtains carboxylic acids of less carbon atoms than the feed alkanol. However, we have found that temperatures of about 50°–75°C., are especially preferable for the one-stage oxidation process of the present invention and without any substantial amount of the 3-methylene-1,5-pentanediol or 3-methyl-3-buten-1-ol feed being converted to molecules of less carbon atoms than the feed.

We have found that nitrogen dioxide is generated in sufficient amount during the nitric acid oxidation at temperatures above about 45° C. so that after the startup period, at which time nitrogen dioxide is desirably added to avoid explosion hazards and help to achieve good yields, further nitrogen dioxide generally does not need to be added. The amount of nitrogen dioxide generated in the reaction at a temperature between about 45°–85° C. is more than about 0.005 mol percent nitrogen dioxide (as $N_2O_4$) based on nitric acid in the reaction zone and typically is between about 0.1 to 0.6 mols per mol of $HNO_3$ charged to the reaction.

In accordance with the two-stage oxidation embodiment of our invention preferably the feed unsaturated compound selected from 3-methylene-1,5-pentanediol or 3-methyl-3-buten-1-ol and their esters is contacted in a first stage at a temperature in the range from about −10° to 85° C. with 1 to 8 mols nitrogen dioxide per mol unsaturated compound to obtain a nitroso-nitrato reaction product of the unsaturated compound and nitrogen dioxide, and the reaction product of the first stage is reacted in a second stage with 2–50 mols of nitric acid per mol of the reaction product at a temperature in the range 30° to 120° C. to convert the reaction product of the first stage to citric acid or citramalic acid. Preferably the temperature used in the first stage of the two-stage process is about −10° to 30° C.

| PREFERRED CONDITIONS, CITRIC ACID PRODUCTION | | | | | |
|---|---|---|---|---|---|
| | Nitric Acid[1] | | $N_2O_4$[1] | | |
| | Concentration Wt. % | Mols-per mol diols | Mols per mol diols | Temp. ° C | Time, Minutes |
| Two-Stage Oxidation Process | | | | | |
| First Stage | | | | | |
| Preferred | 30 to 90 | 2 to 50 | 1 to 8 | −10 to 30 | 2 to 60 |
| Most Preferred | 40 to 75 | 20 to 50 | 2 to 4 | 0 to 20 | 5 to 30 |
| Second Stage | | | | | |
| Preferred | 30 to 90 | 2 to 50 | .005 to 1[2] | 50 to 80 | 240 to 30 |
| Most Preferred | 40 to 75 | 30 to 50 | | 60 to 80 | 120 to 60 |
| Single Stage Oxidation Process | | | | | |
| Preferred | 30 to 90 | 2 to 50 | .005 to 1[2] | 40 to 85 | 240 to 30 |
| Most Preferred | 40 to 75 | 30 to 50 | | 50 to 70 | 120 to 60 |

Notes:
[1]$N_2O_4$ and $HNO_3$ based on total olefinic diols, not just the 3-methylene-1,5-pentane-diol.
[2]It is not necessary to add $N_2O_4$ in the Second Stage of the Two-Stage Process nor in the Single-Stage Process if the process is continuous as small amounts of $N_2O_4$ will be generated in situ.

PREFERRED EMBODIMENT OF THE INVENTION

In a preferred embodiment an aqueous solution of nitric acid and nitrogen dioxide ($N_2O_4$) is charged to a corrosion-resistant reactor, for example a glass-lined vessel fitted for reflux and temperature control, and 3-methylene-1,5-pentanediol is added portionwise to the solution. For each mol of the feed compound to be oxidized the solution should contain about 0.4 mols of the dioxide, but may contain more, e.g., about 4 mols, about 40 mols of nitric acid, and sufficient water to yield a nitric acid concentration of about 70%

(weight). Prior to the addition of the feed, the solution is heated to about 50° C. and this temperature is maintained during the addition period and for about 2 hours after addition is complete.

The excess nitric acid and the dissolved nitrogen oxide by-products are separated from the crude reaction product mixture by use of a falling film evaporator. The residue is usually a viscous light yellow-colored liquid composed mainly of citric acid and oxalic acid. The latter is a by-product of the reaction and oxidation of feed impurities.

For the separation and recovery of the product in the form of the sodium salt, the solid obtained from the flash evaporation of the nitric acid, water, etc., is dissolved in fresh water in an amount sufficient to yield about a 30 weight percent solution. Sufficient calcium hydroxide is then added to the solution for the neutralization of the oxalic acid in the product mixture. Calcium oxalate is an insoluble salt and precipitates from the solution. After separation of the precipitated calcium oxalate by filtration, additional calcium hydroxide is added to the filtrate for the neutralization of the citric acid. A pH of about 9 is required for a complete neutralization. Calcium citrate is also relatively insoluble in water and a second precipitate is formed. Before the calcium citrate solid is recovered by filtration, the solution is heated to facilitate complete neutralization of the acid. The precipitated calcium citrate is collected by filtration and added to a solution of sodium carbonate. The calcium is precipitated in the form of the calcium carbonate salt and this material is also separated by filtration and is discarded. Finally, the desired sodium citrate salt is obtained by concentration and cooling of the aqueous filtrate (see, for example, U.S. Pats. Nos. 2,159,155 and 2,193,904). Citric acid may also be recovered by crystallization.

FEED COMPOUNDS 3-methylene-1,5-pentanediol is in general the most advantageous feed for the production of citric acid in the present process. Usually and because of the difficulties involved in purification of the products of reaction of isobutene and formaldehyde, this diol with contain some 1,5-dihydroxy-3-methyl-pentene-2.

Other useful feeds include the lower carboxylic acid esters of the pentanediol, for example the diacetate, dipropionate and dipivalate esters, as well as the corresponding half-esters. The 3-methylene-1,5-pentanediol linear formal (I, below) and the hemi-formal (II) and their esters, such as acetates, can be used as feeds.

$$CH_2(OCH_2CH_2\underset{\underset{CH_2}{\|}}{C}CH_2CH_2OH)_2 \quad (I)$$

$$HOCH_2CH_2\underset{\underset{CH_2}{\|}}{C}CH_2OCH_2OH \quad (II)$$

Likewise, the cyclic formal derivative of the diol is contemplated for use herein. The cyclic formal or methylenedioxy derivatives are frequently obtained by the acid-catalyzed reaction of 3 mols of formaldehyde per 1 mol of olefin, for example isobutene:

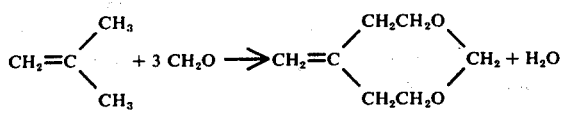

The 3-methylene-1,5-pentanediol feed required for the citric acid process may be obtained from the condensation of 2 mols of formaldehyde with isobutene [See, for example, U.S. Pat. No. 2,789,996 and Blomquist and Verdol, JACS, Volume 77, page 78 (1954).] A particularly preferred method for obtaining the 3-methylene-1,5-pentanediol feed required for the process of the present invention is the method of condensing formaldehyde with isobutene as described in commonly assigned application Ser. No. 458,625, the disclosure of which application is incorporated herein by reference.

In accordance with the embodiment of the present invention directed to citramalic acid production, the desired 3-methyl-3-buten-1-ol feedstock can be produced by the reaction of formaldehyde or a formaldehyde precursor with an olefin such as isobutene. When the olefin-formaldehyde reaction is carried out with an excess of formaldehyde, both cyclic and linear oxymethylene derivatives are formed. Either one of these mixtures are satisfactory feeds for this purpose because upon oxidation the same type of polybasic acid is produced.

The acyloxy-type feed stocks may be obtained from the same reaction carried out in a low molecular weight fatty acid/fatty acid anhydride solvent system. The cyclic formal or methylenedioxy derivatives are frequently obtained by the acid catalyzed reaction of 3 mols of formaldehyde per 1 mol of olefin, for example, isobutene:

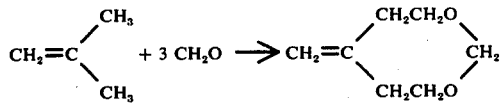

The 3-methyl-3-buten-1-ol feed required for the citramalic process can be obtained from the condensation of 1 mol of formaldehyde with 1 mol of isobutene. (See, for example, U.S. Pats. Nos. 3,574,773 and 2,334,027.)

REACTION CONDITIONS

The oxidation reaction may be carried out in two substantially distinct stages, i.e., Stage 1, the addition of nitrogen dioxide (in the form of dinitrogen tetroxide) across the double bond of the olefin followed by a stage 2 oxidation with nitric acid.

The first-stage oxidative addition is believed to be summarized as follows:

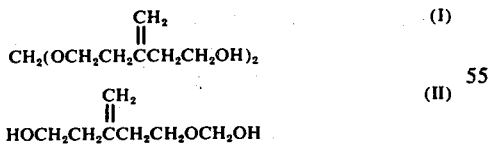

1)

In the second stage oxidation the primary hydroxyl- and nitrosobearing carbon atoms of the feed compound are oxidized to carboxyl groups, e.g., $$-CH_2OH + (O) \rightarrow -CO_2H + H_2O + NO_x \quad 2)$$

$$-CH_2NO + (O) \rightarrow -CO_2H + H_2O + NO_x \quad 3)$$

Also in the second stage the oxynitro (nitrato) group is hydrolyzed to a hydroxy group, e.g.,

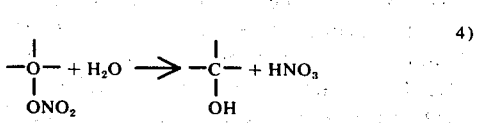

In such a two-stage process, the temperature of each stage may be the same or different. Frequently the process is carried out in two temperature stages:
1. a low temperature stage; and
2. a relatively high temperature stage.

In the first stage the carbon-carbon double bond of the hexenediol feed is oxidized by the addition of nitrogen dioxide ($N_2O_4$) to the double bond. A temperature in the range below 30° C., usually in the range −10° C. to 30° C., preferably in the range 0° C. to 25° C., may be used. Higher temperatures may be used for the oxidative addition, and at temperatures above about 85° C. a super-atmospheric pressure is required in order to maintain $N_2O_4$ in the liquid phase.

In the second stage an elevated temperature is preferred, broadly a temperature in the range of 30° C. to 120° C., preferably in the range 60° C. to 80° C. Thus broadly, the process of the invention may be accomplished a reaction temperatures in the range from −10° C. to 120° C.

As a practical matter, however, the oxidation stages need not be separated and the organic feed stock is charged directly to a mixture of nitric acid and nitrogen dioxide at a temperature within the range of −10° C. to 120° C., preferably in the range of 45° C. to 85° C. Under these conditions, the reaction is considered to be occurring in two separate chemical steps, essentially the same two steps as described above. The temperature may be maintained constant throughout such a reaction, or it may be changed within the range given. The onestage process in the present invention can be carried out in more than one serially connected reactor vessel and at somewhat differing temperature levels particularly due to the exothermicity of the oxidation reaction. However, the one-stage process does not use a separate "stage" or discrete reaction zone wherein substantially only nitrogen dioxide is reacted with the unsaturated diol feed.

NITRIC ACID

The use of nitric acid is an important aspect in the process of the present invention. Although the oxidation of the carbon-carbon double bond by the addition of nitrogen dioxide can be carried out in the absence of nitric acid (see equation 1), the yield of acid is substantially better with nitric acid in the reaction mixture. But the concentration of nitric acid must be low enough to avoid appreciable side reactions.

The concentration of the nitric acid is a governing factor in the second stage of the process. If the concentration is too low, the oxidation rates are unsatisfactory and little or no acid can be produced. If the concentration is too high, the main product is not the desired acid but is an undesirable byproduct. Broadly, nitric acid concentrations in the range from 30% to 90% (weight), based upon total solution, are satisfactory for the process. Better results are, in general, experienced when the range is 40 to 75%, preferably 50 to 70%.

As the oxidation proceeds, the nitric acid concentration drops. Fresh nitric acid may be added, if desired, to maintain a higher and more effective concentration. Another helpful expedient is to carry out the oxidation in the presence of added oxygen gas, for example by introducing air into the reaction vessel (see, for example, British Patents No. 1,110,474 and No. 1,131,447). In this case, the nitric oxide by-product produced in the course of the oxidation is converted to nitric acid.

The amount of nitric acid needed in the process varies depending upon the concentration of the acid. Broadly, an amount in the range of from 2 to 50 mols of nitric acid per mol of hydroxy or hydroxy derivative in the feed is satisfactory, for example one mol of diol feed requires 20 to 40 mols of nitric acid. A larger relative amount is necessary where an oxidizable impurity is present in the feed. The presence of an excess, for example as much as a twenty-fold excess, is satisfactory because recovered nitric acid may be advantageously recycled to the process. The preferred method of operation is to use a sufficient excess of nitric acid to permit the nitric acid content after reaction to remain at a 10–45% concentration in the product.

NITROGEN DIOXIDE REQUIREMENTS

The amount of nitrogen dioxide ($N_2O_4$) needed for the oxidation of the double bond is theoretically one mol. However, in the substantially distinct two-stage oxidation process a larger relative amount should be added, particularly if water is present, because nitrogen dioxide is also used up in a side reaction with water in which nitric oxide and nitric acid is produced. The latter is required for the oxidation of the primary hydroxyl and nitroso groups to carboxyl groups. The nitric oxide can be recovered for the process, as noted above, by reaction with oxygen gas. Broadly, an amount of nitrogen dioxide ($N_2O_4$) in the range 1 to 8 mols per mol of feed is satisfactory. The preferred relative amount is in the range from 2 to 4 mols. For purpose of calculation of the mols of nitrogen dioxide ($N_2O_4$), the $N_2O_4$ form is used.

On the other hand, in the one-step or "one-stage" oxidation process, nitrogen dioxide is generated during the nitric acid oxidation. Therefore, only a small, catalytic amount is needed in the original oxidizing solution. The amount of nitrogen dioxide initially present should be sufficient to prevent explosive nitric acid oxidations. For this purpose 0.005 mol percent based on nitric acid is satisfactory; e.g., 0.005 to 1 mol nitrogen dioxide per mol nitric acid can be used, however it is preferred to use 0.01 to 0.05 mol percent nitrogen dioxide in nitric acid as the oxidizing medium.

REACTION TIME

In the two-stage oxidation process, the time required for the first and low-temperature stage is only the time required for the mixing of the reactants. In general, the period for mixing will be in the range below 15 minutes.

For the reaction at the elevated temperatures the time varies, in general, depending upon the temperature employed. At 120° C. the reaction time should be about 1 minute and should include a subsequent quenching as by cooling or dilution with water. At 30° C., on the other hand, a satisfactory reaction time will be about 6 hours and even longer.

In the one-stage oxidation process, the time of reaction is within the same range, i.e., from about 0.01 to 6 hours; although much longer times may be required for reaction at temperatures below 10° C.

REACTION MEDIUM

The reaction is carried out by mixing the unsaturated alcohol or a solution of the alcohol in water or other inert solvent with an aqueous nitric acid solution. Typically the unsaturated alcohols useful in this process are obtained in aqueous solution and are used without drying. Anhydrous alcohols may also be used as a feed stock, in which the reaction medium is the water of the aqueous nitric acid. In addition to water, acetic acid and other lower organic acids, such as propionic, butyric, pivalic, and chloroacetic acid may be employed. Acetic acid is a convenient solvent where the feed compound is the diacetate derivative of the diol, for example where the diacetate was produced by the method disclosed by Blomquist and Verdol, noted above. In this case the crude reaction product from the isobutene formaldehyde diaddition reaction can be the process feed. Water is the preferred solvent.

EFFECT OF VANADIUM CATALYSTS

As indicated above under "Background of the Invention" vanadium catalysts have been suggested in the past for catalyzing the reaction of isobutene with nitrogen dioxide/nitric acid to produce alpha-hydroxy isobutyric acid. See, for example, Robertson et al. U.S. Pat. No. 2,847,465. Also, vanadium catalysts have been suggested for oxidation of alcohols to carboxylic acid using nitric acid. See, for example, Washecheck Belgian Patent 775,729.

Surprisingly we have found that in the process of the present invention essentially no critic acid product is recovered if the process of the present invention is carried out in the presence of significant amounts of vanadium. Any citric acid which is formed in the presence of a vanadium catalyst has been found by us to be effectively decomposed by the vanadium catalyst so that no significant yield of citric acid is recovered from the process.

In accordance with a preferred embodiment of the present invention the nitric acid contacting step is carried out in the absence of any substantial amount of vanadium. The amount of vanadium in accordance with this embodiment preferably is maintained at less than 0.05 weight percent (500 ppm) of the feed to the reaction zone wherein the oxidation with nitric acid is carried out, more preferably less than 30 ppm of the feed and most preferably less than 5 ppm of the feed by weight. The term "substantial amount of vanadium" is used herein to mean an amount of vanadium above about 5 ppm based on the feed necessary to fill the reaction zone wherein the nitric acid oxidation is carried out. The feed includes the diol feed, nitric acid solution feed and any $N_2O_4$ in the feed.

Vanadium catalysts or species which particularly are to be excluded from the reaction zone in accordance with the present embodiment are those wherein the vanadium is in the +5 valence state such as ammonium metavanadate and $V_2O_5$. These pentavalent species are ones we have particularly found are advantageously excluded from the nitric acid oxidation step of the citric acid synthesis process of the present invention. Also vanadium in lower valence states such as vanadium +3 or +4 is desirably excluded; the lower valence vanadium will be oxidized to pentavalent vanadium by the nitric acid used in the nitric acid oxidation step.

EXAMPLES

The following examples will serve to illustrate the invention, but they are not to be considered as limiting.

The feed used in the examples 1 through 9 was obtained from the addition of two mols of formaldehyde to isobutene. It was mainly 3-methylene-1,5-pentanediol but contained roughly 20 weight percent of 1,5-dihydroxy-3-methylpentene-2 and minor amounts of unidentified by-products of the formaldehyde condensation reaction. While the presence of these materials was undesirable in view of the added consumption of nitric acid and nitrogen dioxide in the process, no undue interference with the process was experienced. These examples illustrate a two-stage oxidation process where very little nitrogen dioxide is generated during the nitric acid oxidation during the initial addition of feed to the $N_2O_4$.

The reaction product mixtures of the examples were converted to the methyl ester derivatives and analyzed using a gas-chromatographic column. For the esterification, the crude reaction product, after removal of the excess nitric acid and water, was dissolved in a 40% (weight) solution of sulfuric acid in methanol and heated at the reflux temperature. Concentrated aqueous ammonium sulfate was used to salt out the ester which was extracted and taken up by chloroform. Aliquots of the chloroform solution were then analyzed by gas chromatography using a 5 foot × ⅛ inch column charged with 100–200 mesh diatomaceous earth (3% ethylene glycol adipate) and with triethyl citrate as the internal standard.

The conditions and results are listed in Tables I and II below.

The procedure used in the examples can be somewhat further illustrated as follows with respect to example No. 1. First an aqueous solution of nitric acid containing 141 g. of nitric acid was charged to a stirred vessel at 0° C and also 8.7 g. of nitrogen dioxide was charged to the vessel. The vessel was next charged with 4.1 g. of the diol feed.

The 15 minutes referred to in Table II, third column, is the length of time during which the diol was being pumped into the vessel. This time is referred to as the $N_2O_4$ addition to double bond time in Table II. During this time the vessel was stirred and the temperature was maintained at 2° C. by means of cooling water circulating in a jacket around the vessel.

After this 15-minute period, the temperature in the vessel was raised to 29° C. by changing the circulating water in the jacket. The temperature was maintained at 29° C. for 60 minutes, as indicated under "Stage 2" in Table II. A portion of the vessel contents were withdrawn after this 60-minute period and was analyzed and found to contain an amount of citric acid equivalent to 34 wt. % yield based on the diol feed.

After this 60-minute period, the temperature in the vessel was again raised, this time to 50° C., by changing the circulating water in the vessel jacket. Portions of the vessel contents were withdrawn after 30, 60, and 120 minutes at 50° C, and were analyzed and found to contain, respectively, an amount of citric acid equivalent to 85, 95, and 105 wt. % yield based on the diol feed.

TABLE I

| EXAMPLE NO. | FEEDS | | | | | | | | |
|---|---|---|---|---|---|---|---|---|---|
| | OLEFINIC DIOL | | Weight Grams | NITRIC ACID | | | NITROGEN DIOXIDE | | |
| | A,[1]% | B,[2]% | | Conc., Wt. % | Grams | Mols Mol, A+B | Grams | Mols/ Mol, A+B | Mols/ Mol, A |
| 1 | 71.4 | ~15 | 4.1 | 70 | 141 | 46 | 8.7 | 2.7 | 3.5 |
| 2 | 71.4 | ~15 | 3.0 | 60 | 100 | 38 | 6.5 | 2.9 | 4.0 |
| 3 | 70 | 24.5 | 3.9 | 70 | 140 | 49 | 8.7 | 2.9 | 4.0 |
| 4 | 70 | 24.5 | 4.1 | 90 | 38 | 36 | 8.7 | 2.7 | 3.5 |
| 5 | 70 | 24.5 | 3.0 | 70 | 106 | 45 | ~3.3 | ~1.5 | ~2.0 |
| 6 | ~50[3] | ~50[3] | 4.7 | 70 | 106 | 45 | 8.7 | — | — |
| 7 | Citric Acid[4] | | 3.0 | 70 | 90 | — | 1.4 | — | — |
| 8 | 71.4[5] | 15 | 4.1 | 60 | 121 | 34 | 8.7 | 2.7 | 3.5 |
| 9 | 70 | 24.5 | 0.05 | — | 0.0 | — | 0.75 | 19 | 27 |

[1] 3-methylene-1,5-pentanediol.
[2] 1,5-dihydroxy-3-methylpentene-2.
[3] Mostly liacetate of A+B, some mono-acetate.
[4] Stability test. Also 0.10 gr. of ammonium molybdate added.
[5] Ammonium vanadate catalyst added (0.1 gr.). One-tenth gram is 0.75 wt. % of the Diol + $HNO_3$ + $N_2O_4$.

TABLE II

| EXAMPLE NO. | TWO-STAGE RUNS OXIDATIONS | | | | | | | |
|---|---|---|---|---|---|---|---|---|
| | STAGE 1 $N_2O_4$ ADDITION TO DOUBLE BOND | | STAGE 2 NITRIC ACID | | | | | |
| | | | LOW TEMP. | | | HIGH TEMP. | | |
| | Temp., °C | Time, Min. | Temp., °C | Time, Min. | Citric Wt. % | Temp., °C | Time, Min. | Citric Wt. % |
| 1 | 2 | 15 | 29 | 60 | 34 | 50 | 30 | 80 |
| | | | | | | 50 | 60 | 95 |
| | | | | | | 50 | 120 | 105 |
| 2 | 2 | 17 | 60 | 30 | 71 | 71 | 30 | 89 |
| | | | | | | 71 | 60 | 89 |
| | | | | | | 71 | 120 | 89 |
| | | | | | | 71 | 190 | 96 |
| 3 | 18 | 21 | 30 | 60 | 41 | 50 | 60 | 87 |
| | | | | | | 70 | 60 | 92 |
| | | | | | | 70 | 120 | 95 |
| | | | | | | 70 | 225 | 94 |
| 4 | 3 | 19 | 30 | 30 | 0 | 70 | 30 | 14 |
| | | | | | | 70 | 60 | 22 |
| | | | | | | 70 | 120 | 31 |
| | | | | | | 70 | 180 | 33 |
| | | | | | | 70 | 300 | 35 |
| | | | | | | 70 | 540 | 35 |
| 5 | 3 | 18 | 29 | 60 | 21 | 70 | 30 | 78 |
| | | | | | | 70 | 60 | 83 |
| | | | | | | 70 | 120 | 82 |
| 6 | 1 | 31 | 30 | 60 | 17 | 50 | 30 | 68 |
| | | | | | | 50 | 60 | 85 |
| | | | | | | 50 | 150 | 98 |
| 7 | — | — | 69 | 20 | 101 | — | — | — |
| | | | | 90 | 98 | | | |
| | | | | 150 | 96 | | | |
| | | | | 210 | 98 | | | |
| 8 | 3 | 24 | 60–65 | 20–30 | None | 61–71 | 60 | None |
| | | | | | | 61–71 | 90 | None |
| 9 | 4 | 13[6] | 52 | 30 | — | 69 | 120 | 43 |

[6] 0.23 cc of $H_2O$ added after $N_2O_4$ addition completed.

These examples demonstrate that the process of the invention is an effective method for the production of citric acid and citrate salts. Other observations in view of the comparative example include:

| Examples | Remarks |
|---|---|
| a) 1 and 2 | The use of nitric acid concentrations in the range 60–70% (weight) is especially advantageous. |
| b) 2 and 3 | For the nitrogen dioxide addition, the temperature range 0° C. to 25° C. is particularly satisfactory. |
| c) 1 and 4 | If the nitric acid concentration is excessive, i.e., exceed about 85%, the yield of citric acid falls off substantially. |
| d) 1 and 5 | Although some reduction in citric acid yield occurs where the nitrogen dioxide to feel mol ratio is about 1:1.5, good yields of citric acid are indicated at mol ratios as low as 1 to 1, and lower. |
| e) 6 | 3-methylene-1,5-pentanediol and esters of this diol are useful feed compounds for the process. |
| f) 7 and 8 | Appreciable amounts of vanadate salts (Ex. 8) do not catalyze the desired reaction, or at least they prevent the recovery of any citric acid. Contrariwise, as seen from Example 7, molybdate salt did not hinder recovering a high yield of citric acid of around 96–100 wt. %. |
| g) 9 | The first stage oxidation, i.e., the addition of $N_2O_4$ to the carbon-carbon double bond can be effected satisfactorily in the presence of nitric acid or in its absence. In a corollary aspect, this example demonstrates that the addition product per se (see equation 1) is also a useful feed compound for the instant process. |

EXAMPLES 10–15

A mixture of 65% 3-methylene-1,5-pentanediol and 35% 1.5-dihydroxy-3-methylpentene-2 was added over a period of 25–30 minutes to a mixture of nitric acid and nitrogen dioxide at the indicated temperature. The contents of the reaction vessel were stirred at all times during the run. Samples were removed periodically, esterified and analyzed as before. Time of reaction was taken to begin after all the reactants were combined. The results are given in Table III below.

EXAMPLES 16–17

The same mixture as in Example 10, 5.0 grams diluted with 15 grams of water, was charged to the nitric acid, nitrogen dioxide mixture under nitrogen pressure and contained in a 300 ml magnetically stirred autoclave at the indicated temperature. An additional 10 grams of water was added to purge the pump and the lines of any organic feed. The autoclave was vented as necessary to maintain the pressure below 750 psig. Analysis was as before. The results are given in Table III.

-continued

| Time (Min.) | Citric Acid (Mol %) |
|---|---|
| 240 | 66 |

Comparing the results of Example 18 with those of Example 15 shows that copper is an effective catalyst for this oxidation. This again is surprising in contrast to the results when vanadium is present in the nitric acid oxidation step.

EXAMPLES 19 AND 20

Two "single" stage oxidation runs were made, one with and one without vanadium present.

In these runs the feed used was 76% 3-methylene-1,5-pentanediol with the remainder mainly 1,5-dihydroxy-3-methylpentene-2. Five grams of the mixed diol

TABLE III

SINGLE STAGE RUNS

| EXAMPLE NO. | TEMPERATURE °C | DIOLS GRAMS | NITRIC ACID WT. % | NITRIC ACID GRAMS | $N_2O_4$ GRAMS | TIME(2) MIN | CITRIC ACID(1) MOL % |
|---|---|---|---|---|---|---|---|
| 10 | 30–32 | 4.43 | 70 | 139 | 10 | 60 | 28 |
|  |  |  |  |  |  | 120 | 42 |
| 11 | 43 | 4.83 | 70 | 140.6 | 10.5 | 60 | 11 |
|  |  |  |  |  |  | 120 | 14 |
| 12 | 49–52 | 4.96 | 70 | 280 | 11 | 0 | 28 |
|  |  |  |  |  |  | 60 | 59 |
|  |  |  |  |  |  | 120 | 61 |
| 13 | 47–51 | 5.17 | 70 | 140 | 5 | 0 | 21 |
|  |  |  |  |  |  | 30 | 53 |
|  |  |  |  |  |  | 60 | 57 |
|  |  |  |  |  |  | 120 | 64 |
| 14 | 49–52 | 5.17 | 70 | 141 | 1.4(3) | 30 | 42 |
|  |  |  |  |  |  | 60 | 50 |
|  |  |  |  |  |  | 120 | 56 |
| 15 | 49–52 | 5.08 | 56 | 175 | 1.4 | 30 | 28 |
|  |  |  |  |  |  | 60 | 37 |
|  |  |  |  |  |  | 120 | 45 |
| 16 | 88 | 5.0 | 56 | 150 | 4.5 | 10 | 29 |
| 17 | 115–119 | 5.0 | 56 | 150 | 4.5 | 10 | 0.4 |

(1)Based on 3-methylene-1,5-pentane diol in the feed.
(2)Time begins when all reactants were combined.
(3)Recovered 5.4 grams of $N_2O_4$ from the crude product mixture.

| Examples | Remarks |
|---|---|
| 10–18 | Are illustrative of the single-stage, one-temperature process. |
| 12 and 13 | Show excellent yields of citric acid at a constant temperature of 50° C. at two different levels of initial nitrogen dioxide concentrations. |
| 14 and 15 | Show successful oxidations using an oxidizing mixture which contains 0.7 to 1.0 mol of nitrogen dioxide per 100 mols of nitric acid. Furthermore, Example 14 shows that $N_2O_4$ is produced during the reaction. |
| 17 | Shows a small yield of citric acid in 10 minutes at 120° C. This and Example 16 suggest shorter contact times at these higher temperatures. |

EXAMPLE 18

The procedure of Example 15 was repeated except that 5.20 grams of mixed diol feed stock was used and 0.65 gram of cupric nitrate trihydrate [$Cu(NO_3)_2 \cdot 3H_2O$] was added to the reaction mixture. The results were as follows:

| Time (Min.) | Citric Acid (Mol %) |
|---|---|
| 30 | 33 |
| 60 | 48 |
| 120 | 59 |
| 180 | 64 | feed was pumped into a vessel containing 100 cc (142 grams) of 70 wt. % nitric acid and 5 grams of $N_2O_4$. The feed was pumped in over a period of 30 minutes. The time was indicated in Table IV below was counted starting from that point in time after all the feed had been pumped into the reaction vessel. The reactor vessel contents were stirred and the temperature was maintained at about 50° to 53° C after the diol feed was added.

In the first run, example 19, no vanadium was added.

In the second run, example 20, 0.0098 g of $NH_4VO_3$ (ammonium vanadate) was added to the reaction zone at the outset. This corresponds to 30 ppm vanadium by weight.

TABLE IV

| EXAMPLE NO. | Vanadium, ppm | Yield of Citric Acid, Wt. % Based on 3-methylene-1,5-pentanediol in Feed | | |
|---|---|---|---|---|
|  |  | 30 min. | 60 min. | 120 min. |
| 19 | 0 | 80 | 98 | 111 |
| 20 | 30 | 37 | 31 | 17 |

The results in Table IV show that using the process of the present invention quite high yields of citric acid are achieved at 50–53° C and in the absence of any significant amount of vanadium, whereas under the same conditions except for the presence of 30 ppm vanadium only a relatively low yield was obtained.

EXAMPLE 21

Feedstock 3-methyl-3-buten-1-ol, in the amount of 6.74 grams, was added to a mixture of 139.5 grams of 70% nitric acid and 5.0 grams of nitrogen dioxide at a temperature of 50° C. After 2 hours at this temperature the reactants were cooled and 10 grams of crude citramalic acid were isolated by evaporation in a nitrogen stream. From this crude product, there was isolated 4 grams of pure citramalic acid by crystallization from ethyl acetate. It had a neutralization equivalent of 73.9.

As will be evident to those skilled in the art, numerous modifications in this process can be made or followed, having in mind the foregoing disclosure and discussion, without departing from the spirit or scope of the disclosure or from the scope of the invention as defined in the following claims.

We claim:

1. A process for the preparation of citric acid which comprises contacting an unsaturated compound selected from 3-methylene-1,5-pentanediol and its esters and formals with a nitric acid solution in an amount of 2 to 50 mols of nitric acid feed per mol of unsaturated compound feed, and at least 0.005 mol percent nitrogen dioxide based on nitric acid, at a temperature between −10° and 120° C, to thereby oxidize said unsaturated compound to citric acid.

2. A process in accordance with claim 1 wherein the contacting with the nitric acid is carried out in the absence of any substantial amount of vanadium.

3. A process in accordance with claim 1 wherein the amount of nitrogen dioxide is from 0.005 to one mol per mol of nitric acid.

4. A process in accordance with claim 1 wherein the contacting is carried out in one stage at a temperature between about 45° and 85° C.

5. A process in accordance with claim 4 wherein the contacting with the nitric acid is carried out in the absence of any substantial amount of vanadium.

6. A process for the preparation of citric acid from an unsaturated compound selected from 3-methylene-1,5-pentanediol and its esters, wherein two stages are used in the process, which comprises contacting the unsaturated feed compound in a first stage at a temperature in the range from about −10° to 85° C. with 1 to 8 mols nitrogen dioxide per mol unsaturated compound to obtain a nitroso-nitrato reaction product of the unsaturated compound and nitrogen dioxide, and contacting the reaction product of the first stage in a second stage with 2–50 mols of nitric acid per mol of the reaction product at a temperature in the range 30° to 120° C. to convert the reaction product of the first stage to citric acid.

7. A process in accordance with claim 6 wherein the contacting with the nitric acid is carried out in the absence of any substantial amount of vanadium.

8. A process in accordance with claim 6 wherein the unsaturated feed compound is contacted with nitrogen dioxide in the first stage at a temperature in the range from about −10° to 30° C. and wherein 1 to 8 mols nitrogen dioxide is added to the reaction zone per mol of unsaturated compound feed.

9. A process in accordance with claim 6 wherein the contacting in the first stage is carried out in the presence of both nitrogen dioxide and nitric acid.

10. A process in accordance with claim 1 wherein the unsaturated compound is 3-methylene-1,5-pentanediol and the concentration of the nitric acid solution is in the range 30–90 weight percent nitric acid.

11. A process in accordance with claim 6 wherein the unsaturated compound is 3-methylene-1,5-pentanediol and the concentration of the nitric acid solution is in the range 30–90 weight percent nitric acid.

12. A process in accordance with claim 11 wherein the contacting with the nitric acid is carried out in the absence of any substantial amount of vanadium.

13. A process in accordance with claim 1 wherein the concentration of said nitric acid solution is in the range from about 40 to 75 weight percent nitric acid.

14. A process in accordance with claim 6 wherein the concentration of said nitric acid solution is in the range from about 40 to 75 weight percent nitric acid.

15. A process in accordance with claim 1 wherein said nitric acid solution is an aqueous nitric acid solution.

16. A process for the production of citric acid which comprises oxidizing at least one compound selected from the group consisting of 3-methylene-1,5-pentanediol, 3-methylene-1,5-pentanediol diacetate and monoacetate, and a formal of 3-methylene-1,5-pentanediol by nitrating said compound with nitrogen dioxide using 1 to 8 mols of nitrogen dioxide per mol of said compound to obtain a nitrato derivative and maintaining at an oxidation temperature in the range from about 30° C. to 120° C. for a period in the range from about 0.01 to 6 hours an aqueous or acetic acid solution of nitric acid and the nitrato derivative, wherein the amount of nitric acid is 2 to 50 mols of the nitrato derivative and wherein the nitric acid concentration in the solution is in the range from about 30 to 90 weight percent.

17. A process in accordance with claim 16 wherein said compound is 3-methylene-1,5-pentanediol.

18. A process in accordance with claim 16 wherein the nitric acid solution is an aqueous solution having a nitric acid concentration in the range from about 40 to 75 weight percent and the oxidation temperature is in the range from about 60° to 80° C.

19. A process in accordance with claim 16 wherein said nitration is effected in the presence of nitric acid.

20. A process for the preparation of citric acid which consists essentially of contacting an unsaturated compound selected from 3-methylene-1,5-pentanediol and its esters with a nitric acid solution in an amount of 2 to 50 mols of nitric acid feed per mol of unsaturated compound feed, and at least 0.005 mol percent nitrogen dioxide based on nitric acid, at a temperature between −10° and 120° C, to thereby oxidize said unsaturated compound to citric acid.

21. A process in accordance with claim 20 wherein the contacting with the nitric acid is carried out in the absence of any substantial amount of vanadium.

22. A process in accordance with claim 20 wherein the amount of nitrogen dioxide is from 0.005 to one mol per mol of nitric acid.

23. A process in accordance with claim 20 wherein the contacting is carried out in one stage at a temperature between about 45° and 85° C.

24. A process in accordance with claim 23 wherein the contacting with the nitric acid is carried out in the absence of any substantial amount of vanadium.

25. A process for the preparation of citric acid from an unsaturated compound selected from 3-methylene-1,5-pentanediol and its esters which consists essentially of contacting the unsaturated feed compound in a first stage at a temperature in the range from about −10° to 85° C with 1 to 8 mols nitrogen dioxide per mol unsaturated compound to obtain a nitroso-nitrato reaction product of the unsaturated compound and nitrogen dioxide, and contacting the reaction product of the first stage in a second stage with 2 to 50 mols of nitric acid per mol of the reaction product at a temperature in the range 30° to 120° C to convert the reaction product of the first stage to citric acid.

26. A process for the preparation of citric acid which comprises (a) reacting isobutene with formaldehyde to obtain 3-methylene-1,5-pentanediol, (b) contacting the 3-methylene-1,5-pentanediol with a nitric acid solution in an amount of 2 to 50 mols of nitric acid feed per mol of 3-methylene-1,5-pentanediol and at least 0.005 mol percent nitrogen dioxide based on nitric acid, at a temperature between −10° and 120° C, to thereby oxidize said 3-methylene-1,5-pentanediol to citric acid.

27. A process in accordance with claim 26 wherein the contacting with the nitric acid is carried out in the absence of any substantial amount of vanadium.

28. A process in accordance with claim 26 wherein the amount of nitrogen dioxide is from 0.005 to one mol per mol of nitric acid.

29. A process in accordance with claim 26 wherein the contacting is carried out in one stage at a temperature between about 45° and 85° C.

30. A process in accordance with claim 29 wherein the contacting with the nitric acid is carried out in the absence of any substantial amount of vanadium.

31. A process for the preparation of citric acid which comprises (a) reacting isobutene with formaldehyde to obtain 3-methylene-1,5-pentanediol, (b) contacting the 3-methylene-1,5-pentanediol in a first stage at a temperature in the range from about −10° to 85° C with 1 to 8 mols nitrogen dioxide per mol of 3-methylene-1,5-pentanediol to obtain a reaction product of the 3-methylene-1,5-pentanediol and nitrogen dioxide, and contacting the reaction product of the first stage in a second stage with 2 to 50 mols of nitric acid per mol of the reaction product at a temperature in the range 30° to 120° C to convert the reaction product of the first stage to citric acid.

32. A process in accordance with claim 1 wherein the contacting is carried out in one stage at a temperature between about 45° and 85° C and wherein the concentration of nitric acid solution is in the range 30 to 90 weight percent nitric acid.

33. A process for the preparation of citramalic acid which comprises contacting an unsaturated compound selected from 3-methyl-3-buten-1-ol and its esters and formals with a nitric acid solution in an amount of 2 to 50 mols of nitric acid feed per mol of unsaturated compound feed, and at least 0.005 mol percent nitrogen dioxide based on nitric acid, at a temperature between −10° and 120° C., to thereby oxidize said unsaturated compound to citramalic acid.

34. A process in accordance with claim 33 wherein the amount of nitrogen dioxide is from 0.005 to one mol per mol of nitric acid.

35. A process in accordance with claim 33 wherein the contacting is carried out in one stage at a temperature between about 45° and 85° C.

36. A process for the preparation of citramalic acid from an unsaturated compound selected from 3-methyl-3-buten-1-ol and its esters, wherein two stages are used in the process, which comprises contacting the unsaturated feed compound in a first stage at a temperature in the range from about −10° to 85° C. with 1 to 8 mols nitrogen dioxide per mol unsaturated compound to obtain a nitroso-nitrato reaction product of the unsaturated compound and nitrogen dioxide, and contacting the reaction product of the first stage in a second stage with 2–50 mols of nitric acid per mol of the reaction product at a temperature in the range 30° to 120° C. to convert the reaction product of the first stage to citramalic acid.

37. A process for the preparation of citramalic acid from 3-methyl-3-buten-1-ol and its esters, wherein two stages are used in the process, which consists essentially of contacting the unsaturated feed compound in a first stage at a temperature in the range from about −10° to 85° C. with 1 to 8 mols nitrogen dioxide per mol unsaturated compound to obtain a reaction product of the unsaturated compound and nitrogen dioxide, and wherein the reaction product of the first stage is contacted in a second stage with 2–50 mols of nitric acid per mol of the reaction product at a temperature in the range of 30° to 120° C. to convert the reaction product of the first stage to citramalic acid.

38. A process in accordance with claim 37 wherein the unsaturated feed compound is contacted with nitrogen dioxide in the first stage at a temperature in the range from about −10° to 30° C.

39. A process in accordance with claim 37 wherein the contacting in the first stage is carried out in the presence of both nitrogen dioxide and nitric acid.

40. A process in accordance with claim 33 wherein the concentration of said nitric acid solution is in the range 30–90 weight percent nitric acid.

41. A process in accordance with claim 37 wherein the concentration of said nitric acid solution is in the range 30–90 weight percent nitric acid.

42. A process in accordance with claim 33 wherein the concentration of said nitric acid solution is in the range from about 40 to 75 weight percent nitric acid.

43. A process in accordance with claim 37 wherein the concentration of said nitric acid solution is in the range from about 40 to 75 weight percent nitric acid.

44. A process in accordance with claim 33 wherein said nitric acid solution is an aqueous nitric acid solution.

45. A process for the production of citramalic acid which comprises oxidizing at least one compound selected from the group consisting of 3-methyl-3-buten-1-ol and 3-methyl-3-buten-1-ol acetate, and the oxymethylene derivative of isobutene and formaldehyde by nitrating said compound with nitrogen dioxide using 1 to 8 mols of nitrogen dioxide per mol of said compound to obtain a nitroso-nitrato derivative and maintaining at an oxidation temperature in the range from about 30° C. to 120° C. for a period in the range from about 0.01 to 6 hours an aqueous or acetic acid solution of nitric acid and the nitroso-nitrato derivative, wherein the amount of nitric acid is 2 to 50 mols per mols of the derivative and wherein the nitric acid concentration in the solution is in the range from about 30 to 90 weight percent.

46. A process in accordance with claim 45 wherein said compound is 3-methyl-3-buten-1-ol.

47. A process in accordance with claim 45 wherein the nitric acid solution is an aqueous solution having a nitric acid concentration in the range from about 40 to 75 weight percent and the oxidation temperature is in the range from about 60° to 80° C.

48. A process in accordance with claim 45 wherein said nitration is effected in the presence of nitric acid.

* * * * *